US006858012B2

(12) United States Patent
Burns et al.

(10) Patent No.: US 6,858,012 B2
(45) Date of Patent: Feb. 22, 2005

(54) SYSTEM AND METHOD FOR GENERATING EXTERNAL COUNTERPULSATION REPORTS

(75) Inventors: Kenneth L. Burns, Laguna Hills, CA (US); Loren A. Manera, Laguna Hills, CA (US); Alexandria Manera, Laguna Hills, CA (US)

(73) Assignee: Applied Cardiac Systems, Inc., Laguna Hills, CA (US)

( * ) Notice: Subject to any disclaimer, the term of this patent is extended or adjusted under 35 U.S.C. 154(b) by 103 days.

(21) Appl. No.: 10/401,638

(22) Filed: Mar. 28, 2003

(65) Prior Publication Data

US 2003/0216651 A1 Nov. 20, 2003

(51) Int. Cl.[7] .............................. A61B 5/02; A61B 5/04; A61B 17/00; A61H 19/00
(52) U.S. Cl. ....................... 600/483; 600/481; 600/509; 600/513; 601/152; 606/201; 606/202
(58) Field of Search ................................. 600/481, 483, 600/485, 490, 492–496, 300, 301, 500–502, 506, 508, 509, 513, 515; 601/152; 606/201, 202

(56) References Cited

U.S. PATENT DOCUMENTS

| 5,261,031 A | * | 11/1993 | Saito ........................... 345/440 |
| 6,450,942 B1 | * | 9/2002 | Lapanashvili et al. ......... 600/16 |
| 6,450,981 B1 | * | 9/2002 | Shabty et al. ................ 601/150 |
| 6,589,267 B1 | * | 7/2003 | Hui ............................. 606/202 |
| 6,736,786 B1 | * | 5/2004 | Shabty et al. ................ 601/152 |

FOREIGN PATENT DOCUMENTS

WO    WO 200243645 A2 * 6/2002 .......... A61G/13/00

* cited by examiner

Primary Examiner—Robert L. Nasser
Assistant Examiner—Navin Natnithithadha
(74) Attorney, Agent, or Firm—K. David Crockett, Esq.; Crockett & Crockett

(57) ABSTRACT

A system for performing ECP and recording ECP system data, patient cardiac parameter data, and other data, and presenting the data in displays that are accessible to the operator in formats that assist in consistent treatment, interpretation of treatment data, and confirmation of therapeutic effect.

24 Claims, 15 Drawing Sheets

Fig. 3
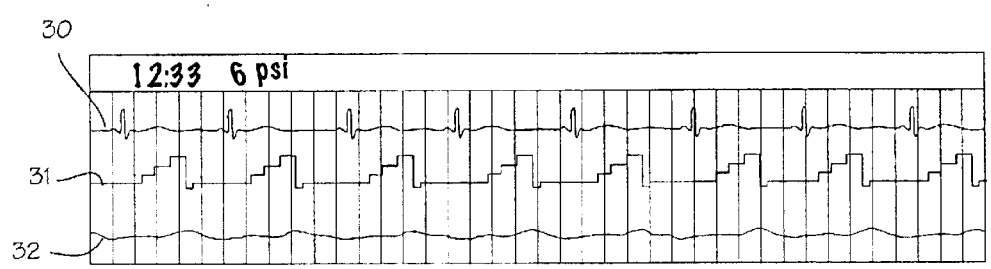
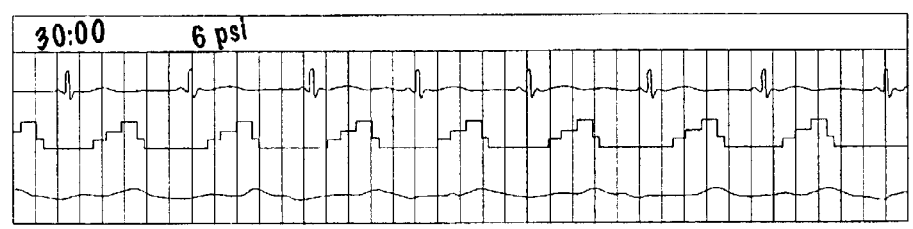
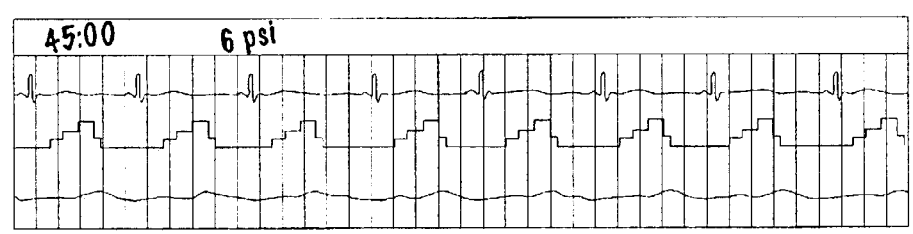

Fig. 4

DAILY TREATMENT RECORD

Patient Name: Marge Innovera  Patient ID: 32453
Physician: Joe Doctor, M.D., F.A.C.C
Treatment: 2 of 4  2/24/2003 at 9:42  Clinician

24-Hour Evaluation (Patient Response)

Angina Episodes: No
1. Amt of Nitro Taken
   Duration of Pain
   Severity (1-10)
   Description
   Activity at the time
2. Amt of Nitro Taken
   Duration of Pain
   Severity (1-10)
   Description
   Activity at the time
3. Amt of Nitro Taken
   Duration of Pain
   Severity (1-10)
   Description
   Activity at the time Medication Changes: No
  If Yes:
Increases in Energy: No
  Desc:
Activity at the time: Ok
  Desc:

Resting Vital Signs / Vital Signs after Treatment

Temp:
BP:  If > 180 Systole and/or > 100 Diastole, Notify MD  BP:
HR:  If < 35 or > 125, notify MD  HR:
Pulse Ox:  If < 90%, do not start treatment and notify MD  Pulse Ox:
Weight  Weight
Cardiac Rhythym: Normal Sinus Rhythm, Bradycardia
Adverse Event During Treatment: No

| | Min | Avg | Max | Inflation Time Utilization | | |
|---|---|---|---|---|---|---|
| Pressure | 8.0 | 8.0 | 8.0 | Available | 780 | mSec |
| P/P Ratio | 0.0 | 0.0 | 0.0 | Utilized | 580 | mSec |
| Total Treament | 00:00 | | | Percentage Utilized | 74.3 | % |

Treatment Notes

Today's Treatment

Resting Vital Signs / Vital Signs after Treatment

Temp:
BP:  If > 180 Systole and/or > 100 Diastole, Notify MD  BP:
HR:  If < 35 or > 125, notify MD  HR:
Pulse Ox:  If < 90%, do not start treatment and notify MD  Pulse Ox:
Weight  Weight
Cardiac Rhythym: Arrhythmias, Tachycardia
Adverse Event During Treatment: No

| | Min | Avg | Max | Inflation Time Utilization | | |
|---|---|---|---|---|---|---|
| Pressure | 8.0 | 8.0 | 8.0 | Available | 780 | mSec |
| P/P Ratio | 0.0 | 0.0 | 0.0 | Utilized | 580 | mSec |
| Total Treament | 00:01 | | | Percentage Utilized | 74.3 | % |

Treatment Notes

Fig. 4a

DAILY TREATMENT RECORD

| Patient Name | Marge Innovera | | Patient ID: | 32453 |
|---|---|---|---|---|
| Physician | Joe Doctor, M.D., F.A.C.C | | | |
| Treatment | 2 of 4  2/24/2003 at 9:42 | | Clinician | |

|  | LEFT | RIGHT |
|---|---|---|
| Calf Cuff Size/Tightness | S, 4 | S, 4 |
| Thigh Cuff Size/Tightness | ML, 5 | ML, 5 |
| Buttock Cuff Size/Tightness | XL, 6 | XL, 6 |

Electrode Placement

Locations Skin Problems and Padding

Anterior    Posterior

| Kind | Location | Description | Treatment |
|---|---|---|---|
| Skin | Post. Left Lateral Lower Thigh | | |
| Skin | Post. Right Medial Upper Thigh | | |
| Skin | Ant. Left Lateral Lower Thigh | | |
| Pad | Ant. Right Mid Waist | | |
| Pad | Ant. Left Mid Waist | | |
| Pad | Post. Left Mid Waist | | |
| Pad | Post. Right Mid Waist | | |
| Pad | Post. Right Lateral Mid Thigh | | |
| Pad | Post. Left Medial Mid Thigh | | |
| Pad | Post. Right Lateral Mid Calf | | |
| Pad | Body | | |
| Pad | Ant. Right Lateral Mid Thigh | | |
| Pad | Ant. Left Medial Mid Thigh | | |
| Pad | Ant. Right Lateral Mid Calf | | |
| Pad | Ant. Left Medial Mid Calf | | |

Fig. 8

| DAILY TREATMENT RECORD TABULAR SUMMARY |||||
| --- | --- | --- | --- | --- |
| Patient Name | Marge Innovera | | Patient ID: | 32453 |
| Physician | Joe Doctor, M.D., F.A.C.C | | | |
| Treatment | 14 of 14 3/14/2003 at 9:42 | Clinician | | |

| TIME | BPM ||| PRESSURE ||| UTILIZATION ||| P/P RATIO ||| TIME | BPM ||| PRESSURE ||| UTILIZATION ||| P/P RATIO |||
| --- | --- | --- | --- | --- | --- | --- | --- | --- | --- | --- | --- | --- | --- | --- | --- | --- | --- | --- | --- | --- | --- | --- | --- | --- |
| | MN | AV | MX | MN | AV | MX | MN | AV | MX | MN | AV | MX | | MN | AV | MX | MN | AV | MX | MN | AV | MX | MN | AV | MX |
| 0:01 | 82 | 82 | 82 | 2.4 | 2.8 | 3.2 | 25 | 31 | 43 | 1.5 | 1.5 | 1.5 | 0:31 | 82 | 82 | 82 | 6.8 | 7.1 | 7.5 | 43 | 56 | 78 | 1.5 | 1.5 | 1.5 |
| 0:02 | 82 | 82 | 82 | 2.4 | 2.8 | 3.2 | 25 | 31 | 43 | 1.5 | 1.5 | 1.5 | 0:32 | 82 | 82 | 82 | 6.8 | 7.1 | 7.5 | 43 | 56 | 78 | 1.5 | 1.5 | 1.5 |
| 0:03 | 82 | 82 | 82 | 2.4 | 2.8 | 3.2 | 25 | 31 | 43 | 1.5 | 1.5 | 1.5 | 0:33 | 82 | 82 | 82 | 6.8 | 7.1 | 7.5 | 43 | 56 | 78 | 1.5 | 1.5 | 1.5 |
| 0:04 | 82 | 82 | 82 | 2.4 | 2.8 | 3.2 | 25 | 31 | 43 | 1.5 | 1.5 | 1.5 | 0:34 | 82 | 82 | 82 | 6.8 | 7.1 | 7.5 | 43 | 56 | 78 | 1.5 | 1.5 | 1.5 |
| 0:05 | 82 | 82 | 82 | 2.4 | 2.8 | 3.2 | 25 | 31 | 43 | 1.5 | 1.5 | 1.5 | 0:35 | 82 | 82 | 82 | 6.8 | 7.1 | 7.5 | 43 | 56 | 78 | 1.5 | 1.5 | 1.5 |
| 0:06 | 82 | 82 | 82 | 2.4 | 2.8 | 3.2 | 25 | 31 | 43 | 1.5 | 1.5 | 1.5 | 0:36 | 82 | 82 | 82 | 6.8 | 7.1 | 7.5 | 43 | 56 | 78 | 1.5 | 1.5 | 1.5 |
| 0:07 | 82 | 82 | 82 | 2.4 | 2.8 | 3.2 | 25 | 31 | 43 | 1.5 | 1.5 | 1.5 | 0:37 | 82 | 82 | 82 | 6.8 | 7.1 | 7.5 | 43 | 56 | 78 | 1.5 | 1.5 | 1.5 |
| 0:08 | 82 | 82 | 82 | 2.4 | 2.8 | 3.2 | 25 | 31 | 43 | 1.5 | 1.5 | 1.5 | 0:38 | 82 | 82 | 82 | 6.8 | 7.1 | 7.5 | 43 | 56 | 78 | 1.5 | 1.5 | 1.5 |
| 0:09 | 82 | 82 | 82 | 2.4 | 2.8 | 3.2 | 25 | 31 | 43 | 1.5 | 1.5 | 1.5 | 0:39 | 82 | 82 | 82 | 6.8 | 7.1 | 7.5 | 43 | 56 | 78 | 1.5 | 1.5 | 1.5 |
| 0:10 | 82 | 82 | 82 | 2.4 | 2.8 | 3.2 | 25 | 31 | 43 | 1.5 | 1.5 | 1.5 | 0:40 | 82 | 82 | 82 | 6.8 | 7.1 | 7.5 | 43 | 56 | 78 | 1.5 | 1.5 | 1.5 |
| 0:11 | 82 | 82 | 82 | 2.4 | 2.8 | 3.2 | 25 | 31 | 43 | 1.5 | 1.5 | 1.5 | 0:41 | 82 | 82 | 82 | 6.8 | 7.1 | 7.5 | 43 | 56 | 78 | 1.5 | 1.5 | 1.5 |
| 0:12 | 82 | 82 | 82 | 2.4 | 2.8 | 3.2 | 25 | 31 | 43 | 1.5 | 1.5 | 1.5 | 0:42 | 82 | 82 | 82 | 6.8 | 7.1 | 7.5 | 43 | 56 | 78 | 1.5 | 1.5 | 1.5 |
| 0:13 | 82 | 82 | 82 | 2.4 | 2.8 | 3.2 | 25 | 31 | 43 | 1.5 | 1.5 | 1.5 | 0:43 | 82 | 82 | 82 | 6.8 | 7.1 | 7.5 | 43 | 56 | 78 | 1.5 | 1.5 | 1.5 |
| 0:14 | 82 | 82 | 82 | 2.4 | 2.8 | 3.2 | 25 | 31 | 43 | 1.5 | 1.5 | 1.5 | 0:44 | 82 | 82 | 82 | 6.8 | 7.1 | 7.5 | 43 | 56 | 78 | 1.5 | 1.5 | 1.5 |
| 0:15 | 82 | 82 | 82 | 2.4 | 2.8 | 3.2 | 25 | 31 | 43 | 1.5 | 1.5 | 1.5 | 0:45 | 82 | 82 | 82 | 6.8 | 7.1 | 7.5 | 43 | 56 | 78 | 1.5 | 1.5 | 1.5 |
| 0:16 | 82 | 82 | 82 | 2.4 | 2.8 | 3.2 | 25 | 31 | 43 | 1.5 | 1.5 | 1.5 | 0:46 | 82 | 82 | 82 | 6.8 | 7.1 | 7.5 | 43 | 56 | 78 | 1.5 | 1.5 | 1.5 |
| 0:17 | 82 | 82 | 82 | 2.4 | 2.8 | 3.2 | 25 | 31 | 43 | 1.5 | 1.5 | 1.5 | 0:47 | 82 | 82 | 82 | 6.8 | 7.1 | 7.5 | 43 | 56 | 78 | 1.5 | 1.5 | 1.5 |
| 0:18 | 82 | 82 | 82 | 2.4 | 2.8 | 3.2 | 25 | 31 | 43 | 1.5 | 1.5 | 1.5 | 0:48 | 82 | 82 | 82 | 6.8 | 7.1 | 7.5 | 43 | 56 | 78 | 1.5 | 1.5 | 1.5 |
| 0:19 | 82 | 82 | 82 | 2.4 | 2.8 | 3.2 | 25 | 31 | 43 | 1.5 | 1.5 | 1.5 | 0:49 | 82 | 82 | 82 | 6.8 | 7.1 | 7.5 | 43 | 56 | 78 | 1.5 | 1.5 | 1.5 |
| 0:20 | 82 | 82 | 82 | 2.4 | 2.8 | 3.2 | 25 | 31 | 43 | 1.5 | 1.5 | 1.5 | 0:50 | 82 | 82 | 82 | 6.8 | 7.1 | 7.5 | 43 | 56 | 78 | 1.5 | 1.5 | 1.5 |
| 0:21 | 82 | 82 | 82 | 2.4 | 2.8 | 3.2 | 25 | 31 | 43 | 1.5 | 1.5 | 1.5 | 0:51 | 82 | 82 | 82 | 6.8 | 7.1 | 7.5 | 43 | 56 | 78 | 1.5 | 1.5 | 1.5 |
| 0:22 | 82 | 82 | 82 | 2.4 | 2.8 | 3.2 | 25 | 31 | 43 | 1.5 | 1.5 | 1.5 | 0:52 | 82 | 82 | 82 | 6.8 | 7.1 | 7.5 | 43 | 56 | 78 | 1.5 | 1.5 | 1.5 |
| 0:23 | 82 | 82 | 82 | 2.4 | 2.8 | 3.2 | 25 | 31 | 43 | 1.5 | 1.5 | 1.5 | 0:53 | 82 | 82 | 82 | 6.8 | 7.1 | 7.5 | 43 | 56 | 78 | 1.5 | 1.5 | 1.5 |
| 0:24 | 82 | 82 | 82 | 2.4 | 2.8 | 3.2 | 25 | 31 | 43 | 1.5 | 1.5 | 1.5 | 0:54 | 82 | 82 | 82 | 6.8 | 7.1 | 7.5 | 43 | 56 | 78 | 1.5 | 1.5 | 1.5 |
| 0:25 | 82 | 82 | 82 | 2.4 | 2.8 | 3.2 | 25 | 31 | 43 | 1.5 | 1.5 | 1.5 | 0:55 | 82 | 82 | 82 | 6.8 | 7.1 | 7.5 | 43 | 56 | 78 | 1.5 | 1.5 | 1.5 |
| 0:26 | 82 | 82 | 82 | 2.4 | 2.8 | 3.2 | 25 | 31 | 43 | 1.5 | 1.5 | 1.5 | 0:56 | 82 | 82 | 82 | 6.8 | 7.1 | 7.5 | 43 | 56 | 78 | 1.5 | 1.5 | 1.5 |
| 0:27 | 82 | 82 | 82 | 2.4 | 2.8 | 3.2 | 25 | 31 | 43 | 1.5 | 1.5 | 1.5 | 0:57 | 82 | 82 | 82 | 6.8 | 7.1 | 7.5 | 43 | 56 | 78 | 1.5 | 1.5 | 1.5 |
| 0:28 | 82 | 82 | 82 | 2.4 | 2.8 | 3.2 | 25 | 31 | 43 | 1.5 | 1.5 | 1.5 | 0:58 | 82 | 82 | 82 | 6.8 | 7.1 | 7.5 | 43 | 56 | 78 | 1.5 | 1.5 | 1.5 |
| 0:29 | 82 | 82 | 82 | 2.4 | 2.8 | 3.2 | 25 | 31 | 43 | 1.5 | 1.5 | 1.5 | 0:59 | 82 | 82 | 82 | 6.8 | 7.1 | 7.5 | 43 | 56 | 78 | 1.5 | 1.5 | 1.5 |
| 0:30 | 82 | 82 | 82 | 2.4 | 2.8 | 3.2 | 25 | 31 | 43 | 1.5 | 1.5 | 1.5 | 0:60 | 82 | 82 | 82 | 6.8 | 7.1 | 7.5 | 43 | 56 | 78 | 1.5 | 1.5 | 1.5 |

Fig. 10

| | GENERAL | PRE | POST | | P/P | BPM | PRESS | UTIL | TREATMENT | | | |
|---|---|---|---|---|---|---|---|---|---|---|---|---|
| | 3/1/200 | BP | 21 | 61 MAX | 3 | 60 | 0.0 | 74.3 | Angina: | +Energy: | Cardiac R. | Arrhy Tachy: |
| 1 | Time 1:00 | HR | 31 | 71 AVG | 0 | 60 | 0.0 | 74.3 | Med Chg: | Skin OK: NO | Adverse Events: | |
| | T: 98.6  Wt 11 | OX | 41 | 81 MIN | 0 | 60 | 0.0 | 74.3 | Blank | | | |
| | 3/14/2003 at 10:03 | BP | 21 | 61 MAX | 2.5 | 150 | 0.0 | 100.0 | Angina: | +Energy: | Cardiac R. | NSR, Brady |
| 2 | Time 00:54 | HR | 31 | 71 AVG | 1.5 | 83 | 0.0 | 60.1 | Med Chg: | Skin OK: NO | Adverse Events: | |
| | Temp 33 Wt 11 | OX | 41 | 81 MIN | 0.9 | 50 | 0.0 | 13.1 | Blank | | | |
| | 3/14/2003 at 10:04 | BP | 21 | 61 MAX | 2.5 | 134 | 0.0 | 100.0 | Angina: | +Energy: | Cardiac R. | |
| 3 | Time 00:47 | HR | 31 | 71 AVG | 1.4 | 102 | 0.0 | 83.7 | Med Chg: | Skin OK: NO | Adverse Events. | |
| | Temp 33 Wt 11 | OX | 41 | 81 MIN | 0.5 | 50 | 0.0 | 20.9 | Blank | | | |
| | 3/14/2003 at 10:04 | BP | 21 | 61 MAX | 2.5 | 176 | 0.0 | 100.0 | Angina: | +Energy: | Cardiac R. | |
| 4 | Time 00:54 | HR | 31 | 71 AVG | 1.6 | 112 | 0.0 | 87.4 | Med Chg: | Skin OK: NO | Adverse Events: | |
| | Temp:  Wt 11 | OX | 41 | 81 MIN | 0.6 | 50 | 0.0 | 18.6 | Blank | | | |
| | 3/14/2003 at 13:47 | BP | 21 | 61 MAX | 2.4 | 135 | 0.0 | 100.0 | Angina: | +Energy: | Cardiac R. | |
| 5 | Time 00:49 | HR | 31 | 71 AVG | 1.4 | 115 | 0.0 | 87.8 | Med Chg: | Skin OK: NO | Adverse Events: | |
| | Temp  Wt 11 | OX | 41 | 81 MIN | 1.0 | 100 | 0.0 | 26.3 | Blank | | | |
| | 3/14/2003 at 13:49 | BP | 21 | 61 MAX | 1.4 | 60 | 0.0 | 100.0 | Angina: | +Energy: | Cardiac R. | |
| 6 | Time 00:00 | HR | 31 | 71 AVG | 1.0 | 60 | 0.0 | 100.0 | Med Chg: | Skin OK NO | Adverse Events. | |
| | Temp  Wt 11 | OX | 41 | 81 MIN | 0.7 | 60 | 0.0 | 100.0 | Blank | | | |
| | 3/14/2003 at 13:51 | BP | 21 | 61 MAX | 2.5 | 151 | 0.0 | 100.0 | Angina: | +Energy: | Cardiac R. | |
| 7 | Time 00:54 | HR | 31 | 71 AVG | 1.7 | 97 | 0.0 | 79.5 | Med Chg: | Skin OK: NO | Adverse Events: | |
| | Temp  Wt 11 | OX | 41 | 81 MIN | 1.0 | 50 | 0.0 | 10.4 | Blank | | | |
| | 3/14/2003 at 13:55 | BP | 21 | 61 MAX | 2.8 | 120 | 0.0 | 100.0 | Angina: | +Energy: | Cardiac R. | |
| 8 | Time 00:45 | HR | 31 | 71 AVG | 1.3 | 93 | 0.0 | 54.3 | Med Chg: | Skin OK: NO | Adverse Events: | |
| | Temp.  Wt 11 | OX | 41 | 81 MIN | 0.1 | 50 | 0.0 | 10.9 | Blank | | | |
| | 3/14/2003 at 13:56 | BP | 21 | 61 MAX | 2.7 | 107 | 0.0 | 100.0 | Angina: | +Energy: | Cardiac R. | |
| 9 | Time 00:57 | HR | 31 | 71 AVG | 1.5 | 93 | 0.0 | 47.2 | Med Chg: | Skin OK: NO | Adverse Events | |
| | Temp: 9 Wt 11 | OX | 41 | 81 MIN | 0.1 | 51 | 0.0 | 13.6 | Blank | | | |
| | 3/14/2003 at 13:59 | BP | 21 | 61 MAX | 1.4 | 64 | 0.0 | 100.0 | Angina: | +Energy: | Cardiac R. | |
| 10 | Time 00:00 | HR | 31 | 71 AVG | 1.0 | 60 | 0.0 | 99.1 | Med Chg: | Skin OK: NO | Adverse Events: | |
| | Temp  Wt 11 | OX | 41 | 81 MIN | 0.8 | 58 | 0.0 | 95.8 | Blank | | | |

SUMMARY OF TREATMENTS
Patient Name   Marge Innovera              Patient ID:   32453
Physician      Joe Doctor, M.D., F.A.C.C
Treatment      35 Treatments from 3/1/03 to 4/5/03

SYSTEM AND METHOD FOR GENERATING EXTERNAL COUNTERPULSATION REPORTS

FIELD OF THE INVENTIONS

The inventions described below relate the field of external counterpulsation.

BACKGROUND OF THE INVENTIONS

External counterpulsation (ECP) is a noninvasive treatment for congestive heart failure, stable and unstable angina pectoris, acute myocardial infarction, cardiogenic shock and other cardiac disease. External counterpulsation refers to the method of squeezing a patient's lower body in syncopation with the patient's heart beat (that is, the lower body is squeezed between each heart beat). To accomplish this, a series of compressive air cuffs are wrapped around each leg; one at calf level, another slightly above the knee and the third on the thigh, and perhaps a cuff over the buttocks. A computerized control system interprets the patient's ECG, and operates valves and an air supply to inflate and deflate the bladders in synchronization with the R-wave of the patient's cardiac cycle. The R-wave represents the start of the diastole, which is the period during which the chambers of the heart expand and fill with blood. During diastole, the air cuffs are inflated sequentially (from the distal bladder on the calves to the proximal bladders on the upper thighs or buttocks), compressing the calves, lower thighs and upper thighs, and all the muscles and blood vessels of the leg. This squeezing action results in an increase in diastolic pressure, generation of retrograde arterial blood flow and an increase in venous return. The cuffs are deflated simultaneously just prior to systole, which produces a rapid drop in vascular resistance to blood flow, a decrease in ventricular workload and an increase in cardiac output.

When used to treat the chronic condition of congestive heart failure, many treatment sessions, spread out over several weeks, are used. A full course of therapy usually consists of 35 one-hour treatments, which may be offered once or twice daily, usually 5 days per week. In the short term, this method of therapy is thought to deliver more oxygen to the ischemic myocardium by increasing coronary blood flow during diastole, while at the same time reducing the demand for oxygen by diminishing the work requirements of the heart. Long-term benefit has been established by numerous studies. While researcher are still trying to determine why the therapy works, research has indicated that the therapy leads to increased coronary collateral flow to ischemic regions of the heart (though the mechanism leading to the effect is unknown). Clinical trials have demonstrated that the beneficial effects of ECP, including increased exercise time until onset of ischemia and a reduction in the number and severity of anginal episodes. These effects are not only sustained between treatments, but may persist for several months or years after the entire course of therapy.

The effectiveness of ECP treatment for chronic conditions is determined by the changes in diastolic pressure, systolic pressure, heart rate observed over the course of treatment. Currently, doctors and clinicians administering ECP to patients review a few strips of ECG and blood pressure data to determine if ECP performed on a particular patient is being performed properly and having a beneficial effect on the patient. Indications of beneficial effect include increased cardiac output, and, depending on the particular cause or manifestation of angina pectoris and/or congestive heart failure improved ECG, lower diastolic blood pressure, and a lower heart rate. Currently, a few paper strips which the operator collects during each session are collected in the patients chart for comparison of cardiac parameters during each session. No other data is collected, because it is not currently used. There is no generally accepted endpoint for the therapy, and no generally accepted method for determining if further therapy would be useful for a particular patient. Hence, the industry has settled on an apparently arbitrary 35 hour course of therapy. The treatment is offered on the basis that the patient will respond to therapy, and that 35 sessions will be sufficient. If a patient is well treated with 35 sessions, all is well and good for that patient. If, however, the patient would benefit from a longer course of treatment, none will be provided because there is no method of identifying these patients. If the patient would have been well treated with substantially less than 35 sessions, the complete 35 session therapy would then be considered to include a substantial amount of unnecessary treatment. The current absence of any mechanism for tracking and analysis makes it impossible to objectively determine if further treatment would be warranted.

SUMMARY

The systems and method described below provide for improved performance of external counterpulsation therapy and improved reporting of the effects of external counterpulsation therapy. When external counterpulsation therapy is provided in multiple sessions to treat chronic heart disease, cardiac parameters are recorded continuously for each session. The parameters and/or pictorial representations are stored in-a computer memory for recall, and may be recalled in formats particularly conducive to ensuring that therapy is applied on a consistent basis, ascertaining the effectiveness of the therapy and its possible endpoint, and identifying trends in patient treatment.

The system is used in conjunction with an external counterpulsation system. The ECP system may be our own NCP-2 ECP system, or systems provided by companies such as Vasomedical or CardioMedics. The system includes several inflatable cuffs for the legs and buttocks of the patient, ECG monitors, blood pressure monitors (plethysmographs), high pressure air supply, valves and actuators, and a computer to control the operator of the system and record system parameters and cardiac parameters reported by the ECG monitors and blood pressure monitors. The system may also include a cardiac output monitoring system and bladder evacuation system.

BRIEF DESCRIPTION OF THE DRAWINGS

FIG. 3 illustrates conventional strips used by doctors to assess the progress of ECP.

FIGS. 4 and 4a illustrate an interactive display provided by the system to track and control external counterpulsation variables.

FIG. 8 is a table of cardiac parameters for an external counterpulsation session.

FIGS. 10 and 10a are tables of ECP system parameters and cardiac parameters for a complete course of ECP therapy.

DETAILED DESCRIPTION OF THE INVENTIONS

Figure 1:
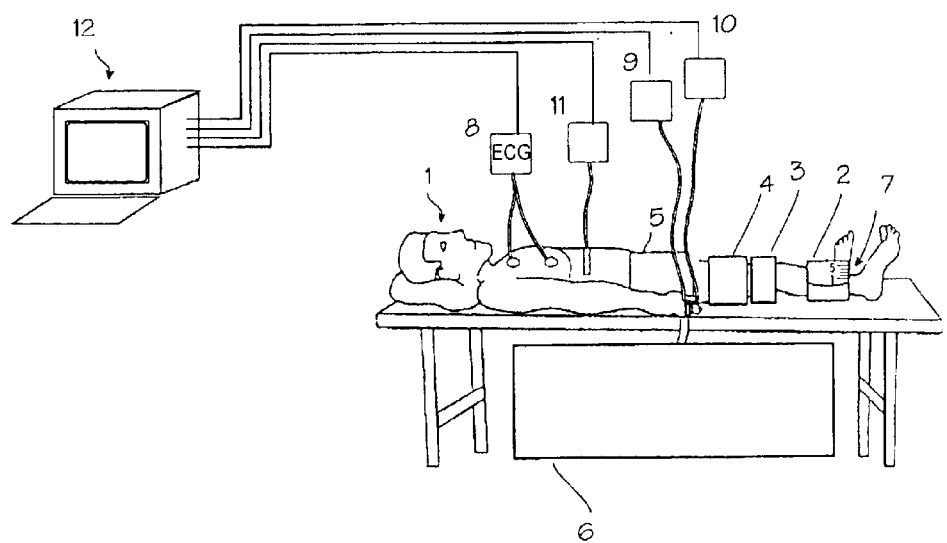
FIG. 1 illustrates an external counterpulsation system.

FIG. 1 illustrates an external counterpulsation system. The system includes several bladders adapted for placement on the patient the patient 1. The bladders 2, 3, 4 and 5 are placed around the legs of the patient, and are operably attached to an inflation and deflation system 6. Each of the bladders is marked with sizing indicia 7, so that the bladders can be fastened to certain and reproducible tightness. An ECG monitoring system 8 and blood pressure monitoring system 9 are operably attached to the patient. A pulse oximetry monitoring system 10 is also attached to the patient. Also, a cardiac output monitoring system 11, such as an impedance cardiograph, may be attached to the patient. A control system 12 includes a computer, a keyboard and input devices, and a display. The computer is programmed to control the inflation and deflation system in response to the patient's ECG, and record ECG data reported from the ECG monitoring system, blood pressure data reported from the blood pressure monitoring system, blood oxygen content data reported by the pulse oximetry monitoring system, and cardiac output data reported by the cardiac output monitoring system. For convenience, ECG data, blood pressure data, blood oxygen data, heart rate and cardiac output may be referred to as cardiac parameters. The control system is also operable to generate displays necessary for an operator interface and generate reports, for display or printing, in predetermined formats as described below.

Figure 2:
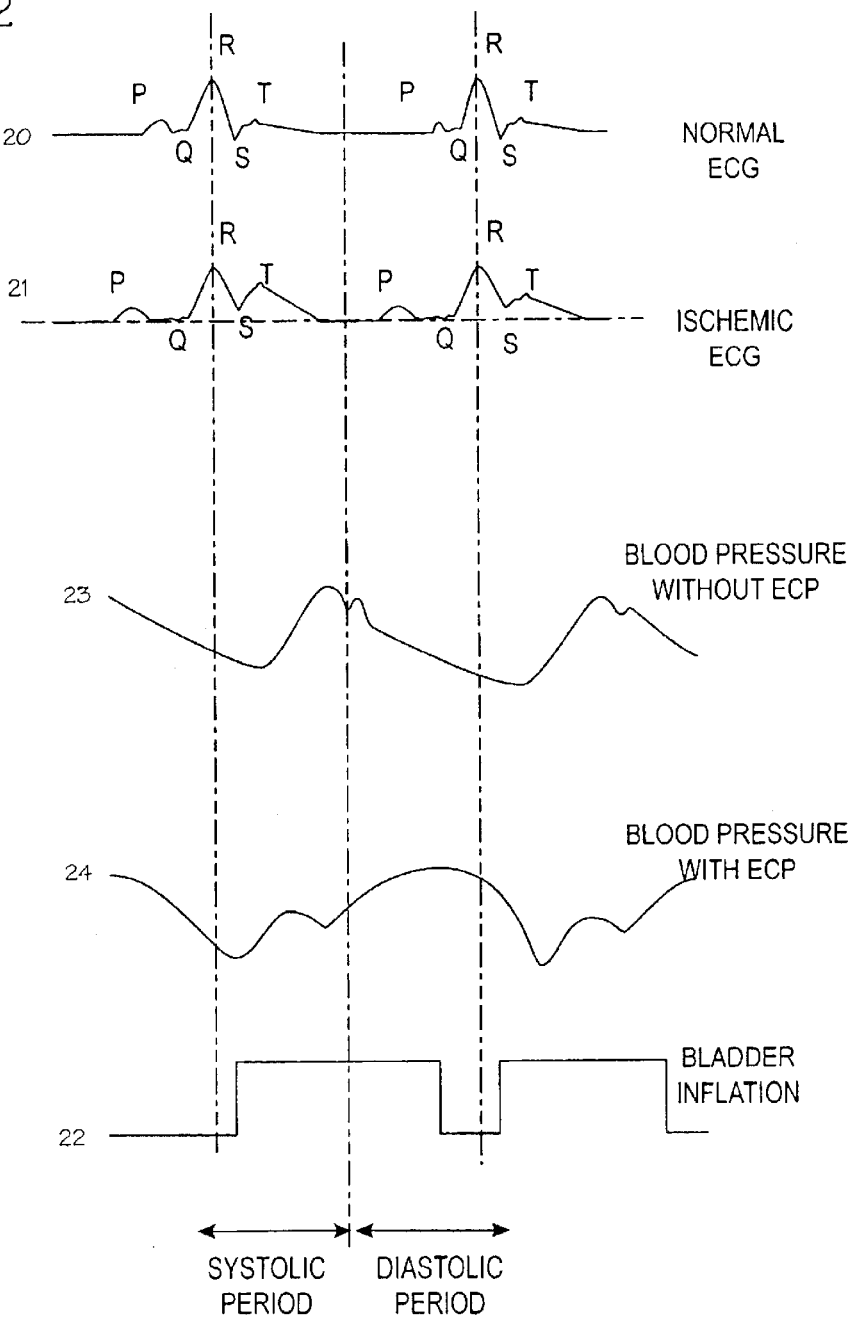
FIG. 2 illustrates the timing of bladder inflation in relation to the patient's ECG to provide ECP therapy.

Operation of the bladders is controlled by the control system so that the bladders are inflated to compress the lower body during the diastolic period of the heartbeat so as to increase blood pressure during the diastolic period to a level higher than systolic pressure. This timing relationship between the heartbeat and the bladder inflation is illustrated in FIG. 2. As illustrated in FIG. 2, the ECG trace 20 is exemplary of a normal patient's ECG, showing the typical Q, R, S, T waves indicative of various stages of the electrophysiological activity of the heart. The P wave represents the start of a heartbeat, specifically the contraction of the atria which initiates the heartbeat. The Q and R waves represent the contraction of the left ventricle. This represents the heartbeat, that is, the systole, in which the heart is forcing blood out into the body. After the R wave peaks, the heart relaxes and the chambers of the heart expand and take in blood. The ST portion of the ECG represents depolarization and re-polarization of the ventricles (the return of the heart to baseline), preparatory to the following heartbeat. ECG trace 21 illustrates the ECG of a particular patient with ischemia, as indicated by the elevated ST wave (every patient will exhibit a different ECG, depending on his particular cardiac ailment). The bladder inflation line 22 indicates that the control system is inflating the bladders after detecting the R wave. The patient's nominal blood pressure, as it would be without external compression, is represented by line 23, which illustrates the systolic blood pressure significantly higher than diastolic blood pressure. The patient's blood pressure during augmentation is shown in line 24, which shows that the systolic blood pressure is lower than the augmented diastolic blood pressure. Counterpulsation is performed with the goal of increasing the ratio of diastolic pressure to systolic pressure from its typical levels (80/120, or 0.75, for example) to a level of about 1.2 (for example, 144 diastolic/120 systolic) or higher. Ratios in the range of 1.0 to 1.5 are observed in patients. The ratio is a commonly used expression of the level of augmentation.

Conventionally, proper performance of external counterpulsation therapy is monitored by reviewing selectively generated strip charts, taking from a very small period within the hour-long session. FIG. 3 illustrates a typical strip chart provided to doctors to report the performance of ECP. These strip charts have previously been generated by an operator, on the fly, during an ECP session. Three such strips are shown in the figure. Each strip includes the patient's ECG trace 30, the system inflation/deflation trace 31, and the patient's blood pressure trace, reported continuously (trace 32). The session time and cuff pressure are hand-written by the operator. This report is useful for ensuring that bladder inflation is occurring during diastole, after the desired delay after the R-wave, and that the counterpulsation is having the desired effect on diastolic blood pressure. It also confirms that the ratio is increased from the normal range to a level above 1.0. However, these strips represent three six-second periods during the course of a session. No record of the rest of the session is generated, and all the patient data lost.

Because counterpulsation therapy requires many sessions, many variables can affect the success of the therapy. To eliminate the significant variables of cuff placement and ECG electrode placement, or to detect variations in the treatment that have caused beneficial or deleterious effects on the therapy, the control system provides a Daily Treatment Record as shown in FIGS. 4 and 4a. The daily treatment record provides a multi-page display 40 which includes a patient identification field 41, fields 42 for entry of patient reported symptoms, a previous treatment information field 43 for display of ECP system parameters such as cuff pressure and utilization percentage (average) for the prior session, and fields 44 for entry of pre-session cardiac parameters measured from the patient immediately before starting an ECP session. The control system is programmed to display previous treatment data and current session ECP parameters in appropriate corresponding sub-fields.

The second page of the display, shown in FIG. 4a, includes a cuff placement field 45, an electrode placement field 46, and a pad placement field 47. In the cuff placement field, the control system accepts input from the operator relating the cuff size used on the patient, and the tightness of the cuff used in the session. As indicated in FIG. 1, the various cuffs are provided in several sizes, and each cuff is provided with indicia indicating the tightness achieved when secured on the patient with different degrees of overlap of the fastening areas. The operator, having selected a suitable size, and having sized the cuffs to the patient, enters the size and tightness in the fields provided. (During the course of therapy, the operator may adjust the tightness of the cuffs (or change the cuff to a different size) as necessary to obtain the desired augmentation, and then enter those changes in the appropriate fields.) During an initial ECP session, the operator will enter the size and tightness of all cuffs used on the patient, and the placement of each of the ECG leads. After the initial therapy session, the control system is operable to call up the patient's recorded data upon instructions from the operator.

In the electrode placement field 46, the control system accepts input from the operator relating to the placement of electrode leads, and presents graphic representation 48 of the patient. A three-electrode ECG is typically used, and the lead may be marked or colored to indicate proper placement. In the display, the electrode icons are colored green, black and white (marked G, B and W in the black and white figure), to correspond to common green, black and white electrodes used for three-lead ECG. The operator, having selected appropriate electrode placement on the patient's body, enters the electrode locations by dragging the icons G, B and W to the corresponding position on the graphic representation of the patient. During an initial ECP session, the operator chooses the electrode sites according the guidelines for the ECG system. In subsequent sessions after the initial therapy session, the control system is operable to call up the patient's recorded data upon instructions from the operator, including the initial session electrode placement and/or electrode placement for any prior session. This assists the operator in maintaining consistency in electrode placement (electrode placement variations will result in ECG distortions, from session to session, making evaluation difficult).

In the pad placement field 47, the control system presents another graphic representation 49 of the patient, with icons representing various pads that are provided for patient comfort. The operator places the pads in the initial ECP session, and may arrange them to make the patient comfortable, and records the preferred pad locations by manipulating the pad icons 50 in the pad placement field so that they appear relative to the patient graphic in positions corresponding to actual placement on the patient. Additionally, any lesions, other patient supports in use, etc. may be recorded with additional icons 51.

Figure 5:
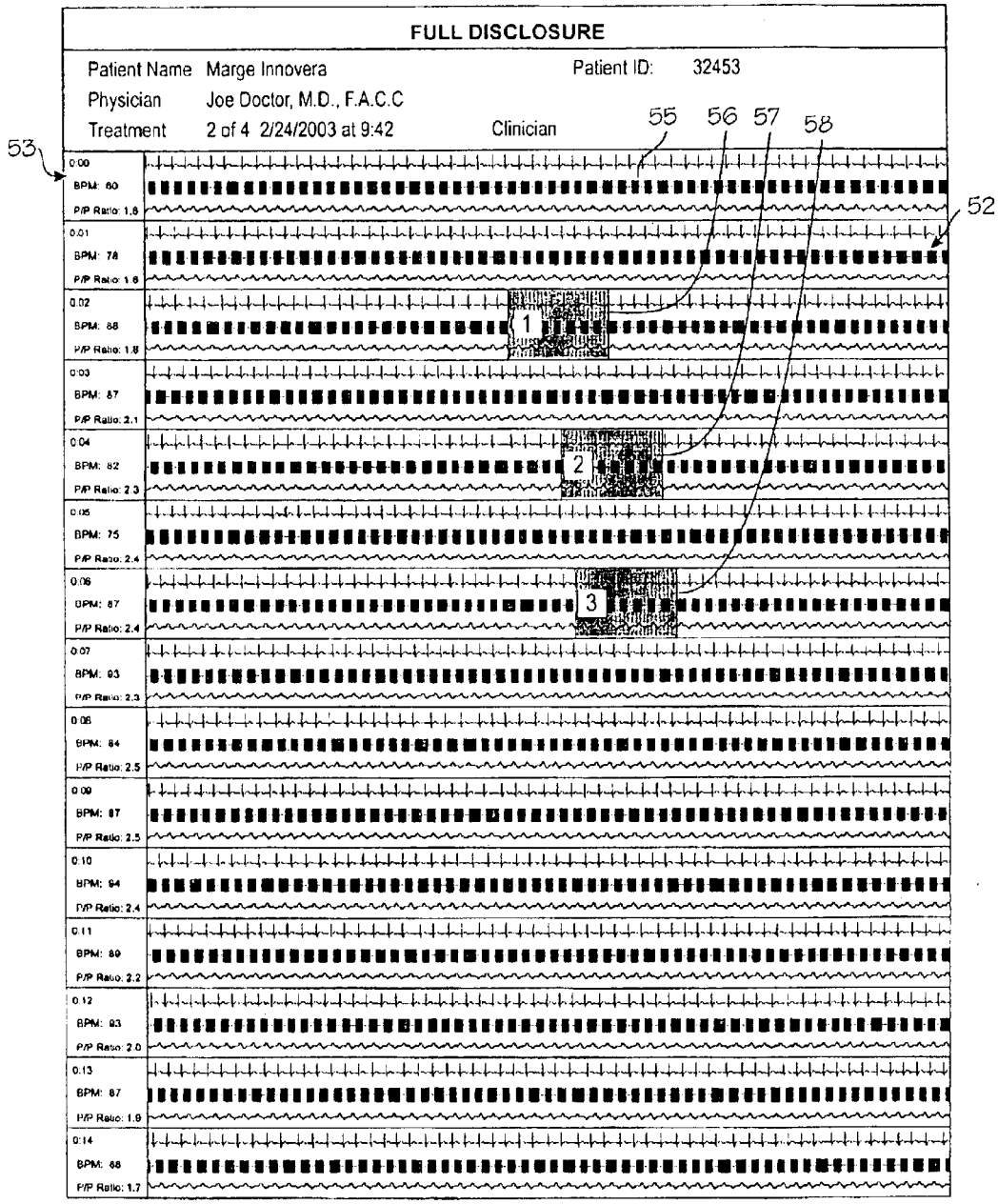
FIG. 5 illustrates the consolidated report of cardiac parameters over a treatment session.

FIG. 5 illustrates a portion of the new report provided by the control system, which may be provided in printed form or on a computer display. The system collects all measured data, collected form the patient and the ECP system, during every session of ECP therapy, and FIG. 5 shows a fifteen-minute portion of the data (the entire report to the session includes four pages) in a formatted table 52. As shown in the figure, full ECG, inflation/deflation time, and augmented blood pressure data is recorded continuously, for the entire ECP session. The ECG data, inflation time data, and blood pressure data are presented in trace format in the numerous trace display fields 53. The session time (in minutes), heart rate (in beats per minute) and ratio are reported in tabular form in tabular data display fields 54. One trace display field and one tabular data display field is provided for each minute of therapy, and these fields report the instantaneous data and averaged data for each minute. Each trace display field includes an ECG trace 30, a blood pressure trace 32, and an inflation/deflation trace 55 comprising a series of compression icons 56. The compression icons report, in easily visible bar graph format, the delay time and inflation time and deflation time provided for every counterpulsation. These three graphical elements are presented in synchronized relationship, so that the temporal relationship between the ECG, counterpulsation, and blood pressure can be easily understood. The date presented represents continuous data for the entirety of the session (notwithstanding the obvious fact that any of the data which is picked up and transmitted digitally is subject to discrete sampling).

Figure 6:
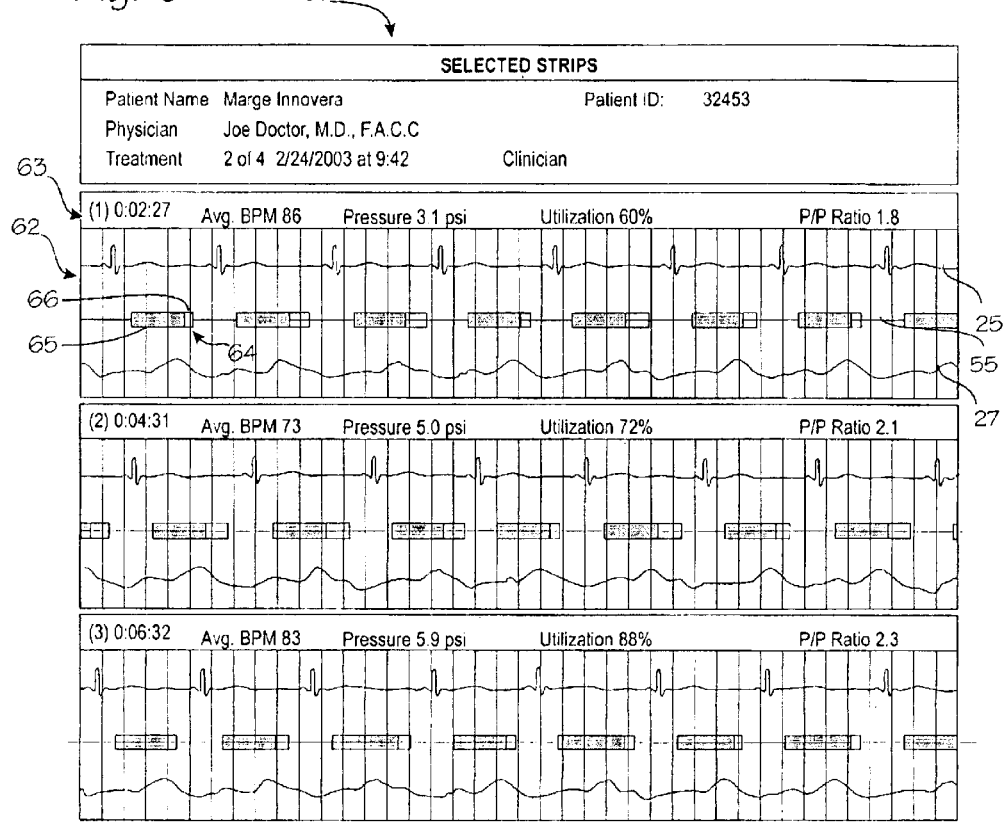
FIG. 6 illustrates a selected strip report provided by the system.

An operator reviewing the report of FIG. 5 may review the entire report, including data for the entire hour-long session, and appreciated data trends that indicate quality of the counterpulsation therapy provided to the patient. The operator may manipulate shaded cursors 57, 58 and 59 to select time periods of particular interest for expansion into a larger format shown in FIG. 6. The cursors are labeled as cursor 1, 2 and 3 (or other distinct indicia) so that they may be correlated to the strips generated for FIG. 6. The cursors are depicted as shaded blocks or windows, but they may be provided in any other form that allows operator manipulation and location of the cursor to be used as an input of the desired time period to be expanded FIG. 6 illustrates a selected strip report generated by the system based on time periods selected by the operator through manipulation of strip selecting cursors 57, 58 and 59. The selected strips display 61 presents the time periods selected in FIG. 5. They are presented in larger scale, for closer analysis of the relationship between the ECG, counter-pulsations, and augmented blood pressure, and include a trace display field 62 and a tabular data field 63. As can be more clearly seen in the figure, the compression icons 64 that make up the inflation/deflation trace 55 comprise two horizontally oriented segments. The first segment 65, indicated in one of the many icons shown in the figure, represents the time in which the bladders are pressurized, and its horizontal extent corresponds to the duration of the inflation of the bladders (the counterpulsation). (The time between the R wave and the start of the compression icon represents the delay enforced by the system between recognition of the R wave and initiation of counterpulsation.) The second segment 66 represents the deflation time, and its horizontal extent corresponds to the time taken to deflate the bladders. (The bladders may be deflated passively, but it is preferable to evacuate the bladders by applying suction, to provide very rapid deflation.) The control system calculates a percentage, which we refer to as the utilization percentage, of the available time for compression during which compression is actually accomplished, and reports this utilization percentage in the tabular data field. Thus, in the various strips shown, the utilization is reported as 60%, 72%, and 88%. The control system also calculates the average cuff pressure applied to the cuffs (in pounds per square inch), the average peak-to-peak ratio, and the average heart rate (in beats per minute).

The utilization percentage is an artificially designated ratio that can be defined in several ways, and we have chosen to calculate based on the available time between R waves (minus the inflation delay of 100 millisecond and the pre-R wave refractory period of 150 milliseconds, imposed based on a prediction of the time of the next coming R wave predicted on a running average of previous R wave intervals). The inflation period includes the time the system is inflating the bladders, and excludes the deflation period. Thus, ratio is calculated by dividing the actual inflation time by the R wave interval less the delay and refractory periods. Utilization percentages of 80% to 90% are preferable, and consistent operation of ECP systems at lower percentages are expected to yield lower therapeutic benefit.

Figure 7:
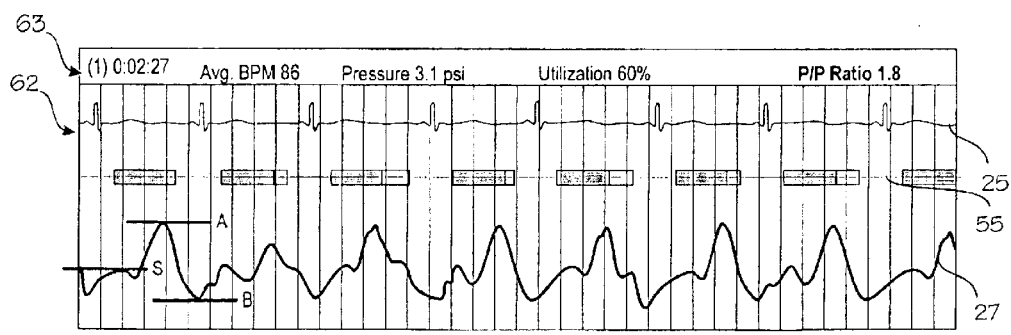
FIG. 7 illustrates an interactive strip display provided by the system.

For closer inspection of the augmentation ratios, the control system generates an interactive display shown in FIG. 7. This display is similar to the selected strips shown in FIG. 6, and includes similar tabular data field and trace display field. Appropriate interface is provided to permit adjustment of the gain on the various traces, so that the vertical scale may be selectively increased or decreased by the operator. In addition, guides A, S and B are provided in the display. These cursors may be manipulated by the operator, and set respectively at the point which the operator decides corresponds to the peak augmented pressure, peak systolic pressure, and the baseline pressure. When the operator sets the cursors, the control system calculates the augmentation ratio for the indicated heartbeat. The calculated ratio is reported in the tabular data field, regardless of the gain applied to the blood pressure trace. The guides may be manipulated with a cursor or handle in the interface, and moved into superimposition on any portion of the blood pressure trace. The control system calculates the ratio based on the pixels of the display, so that the pixel distance between the augmented pressure cursor, systolic pressure cursor and baseline pressure cursor may be made without regard to the gain applied to the image or the absolute pressures involved. Referring back to FIG. 6, the peak-to-peak ratio shown in the data fields may be calculated and entered upon operator input and selection of an exemplary pressure wave, as shown in FIG. 7, or it may be calculated by the control system, based on an average of values calculated from the pressure trace.

Figure 9:
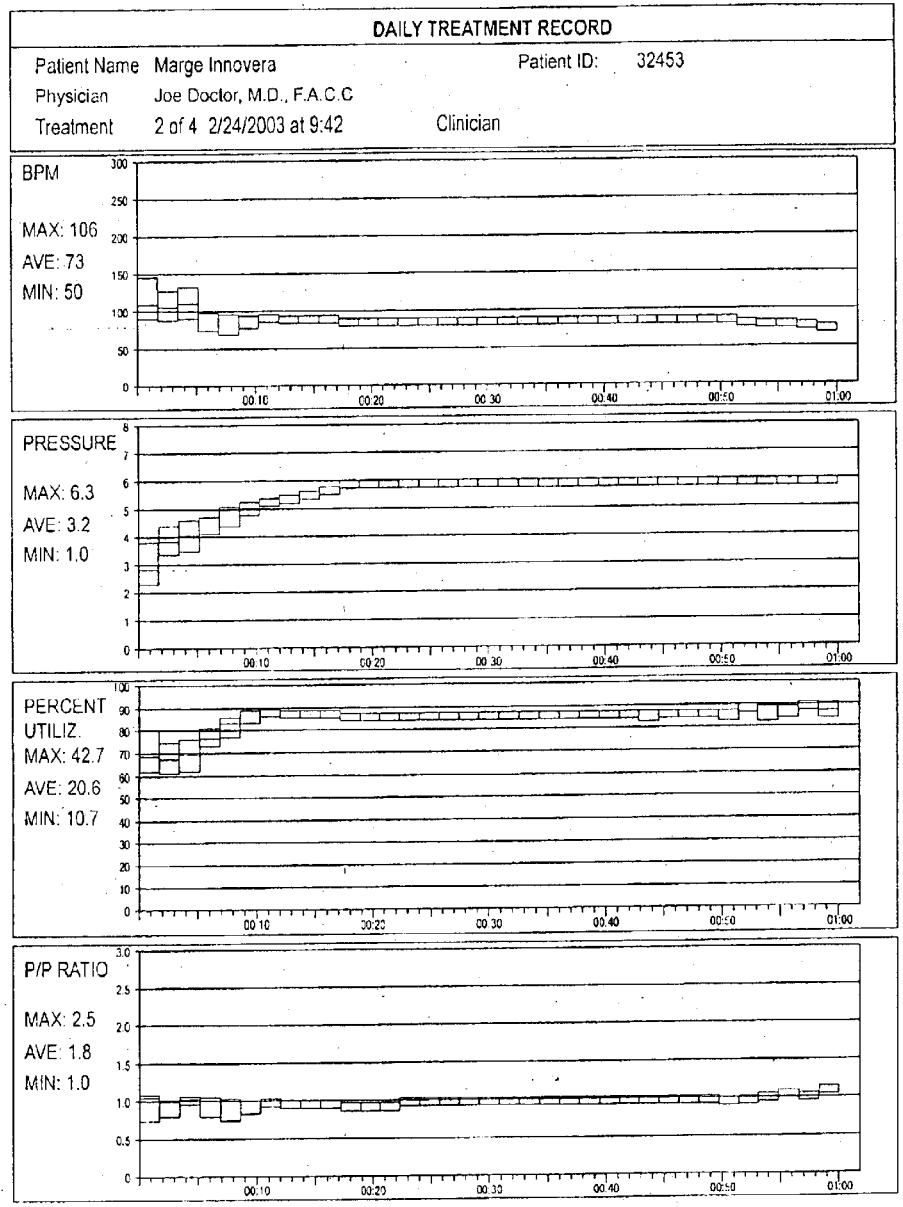
FIGS. 9 and 9a are graphical displays of cardiac parameters for an external counterpulsation session.
Figure 9A:
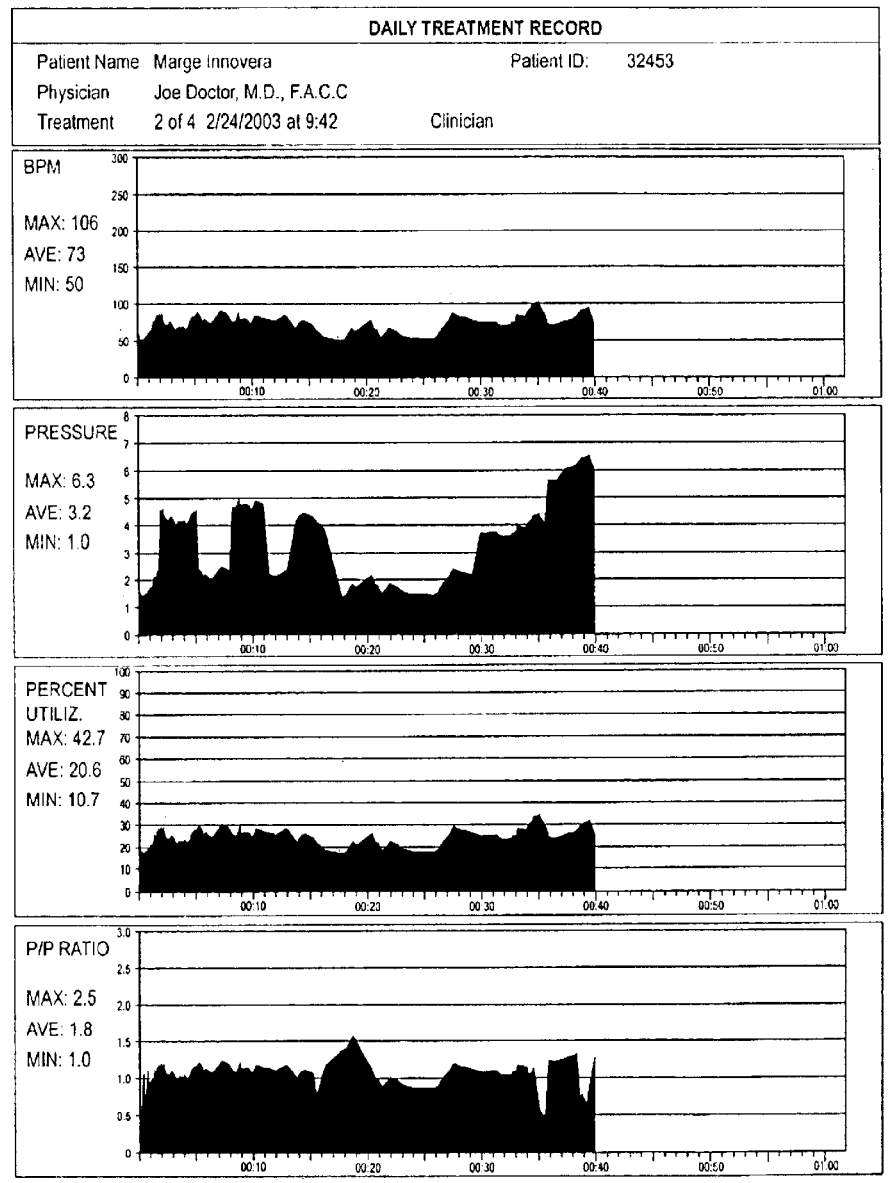

FIGS. 8, 9 and 9a illustrate reports useful for determining session trends in the ECP therapy. FIG. 8 is a table of cardiac parameters for an external counterpulsation session provide a tabular daily treatment record which provides a record of a single ECP session, and includes a table listing minute-by-minute average, maximum, and minimum values of cardiac parameters and system parameters. Heart rate (BPM), cuff pressure, utilization percentage and peak-to-peak ratio are reported for each minute of therapy. Using this chart, the operator may select any reported minute (by movement of a cursor or selecting a data field) and navigate to an expanded report of the time period selected. In response to the selection made by the operator, the control system provides an expanded report, in format such as that illustrated in. FIGS. 9 and 9a illustrate graphical versions of the display of FIG. 8, and include graphs of heart rate (BPM), cuff pressure, utilization, and P/P ratio for a session selected by the operator. Review of FIG. 9 provides the operator with confirmation that heart rate of the patient was acceptable, that cuff pressure was in fact ramped up to 6 psi and maintained at 6 psi for most of the session, that utilization was high for the session. It also indicates that the peak-to-peak ratio is at an expected value, given that the patient identification field at the top of the display indicates that this report pertains to the second ECP session. FIG. 9a present similar data in a different form, and indicates that cuff pressure is unexpected low for much of the session, that utilization is low for much of the session, but peak-to-peak ratio appears normal for an early ECP session. On the basis of this data, the operator may adjust ECP parameters to achieve the desired levels. In both FIGS. 9 and 9a, data fields corresponding to the graphs list the minimum, maximum and average values of the parameter indicated in the graph. These values may pertain to the entire treatment session, or to operator selected time periods. As with the other displays, the time frames may be selected by highlighting a time period, dragging cursor over a time period, or other input means.

Figure 10A:
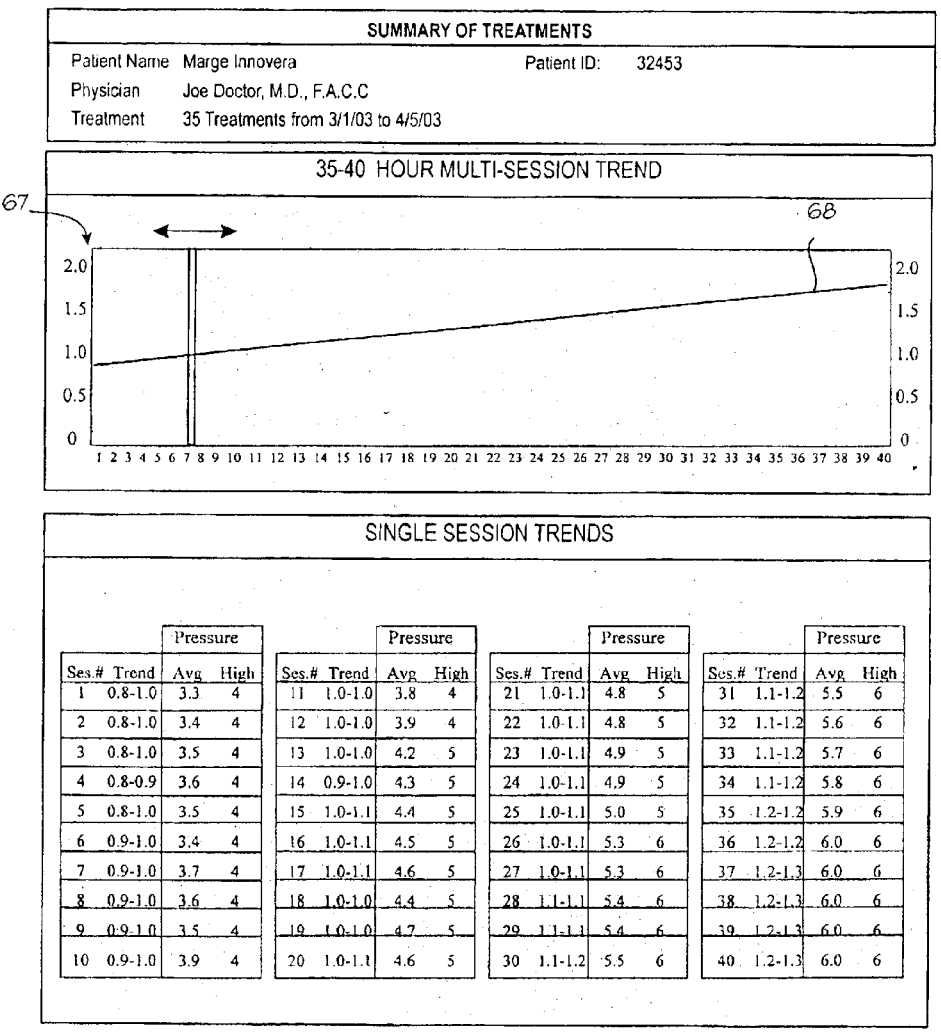

FIG. 10 provides records of augmentation trends of each session, and displays ECP parameters and patient cardiac parameters in tabular form. FIG. 10 also includes fields for reporting self-reported conditions (angina, medicines being taken, skin problems, adverse events, etc.). FIG. 10a provides records of augmentation trends over the entire multi-session therapy, along with augmentation trends of each session (shown in the lower window). FIG. 10a includes a graph of augmentation over time in the multi-session trend field 67, and the trend line 68 immediately conveys the expected upward trend in augmentation ratio. In either Figure, selection of a session by the operator, such as by highlighting of a session (illustrated in FIG. 10) or by movement of a cursor along the trend line, is taken by the control system as the operator input for directing the control system to display a more detailed report of the selection session. In response to the selection, the control system generates a detailed session report such as the reports shown in FIGS. 8, 9 or 9a.

Figure 11:
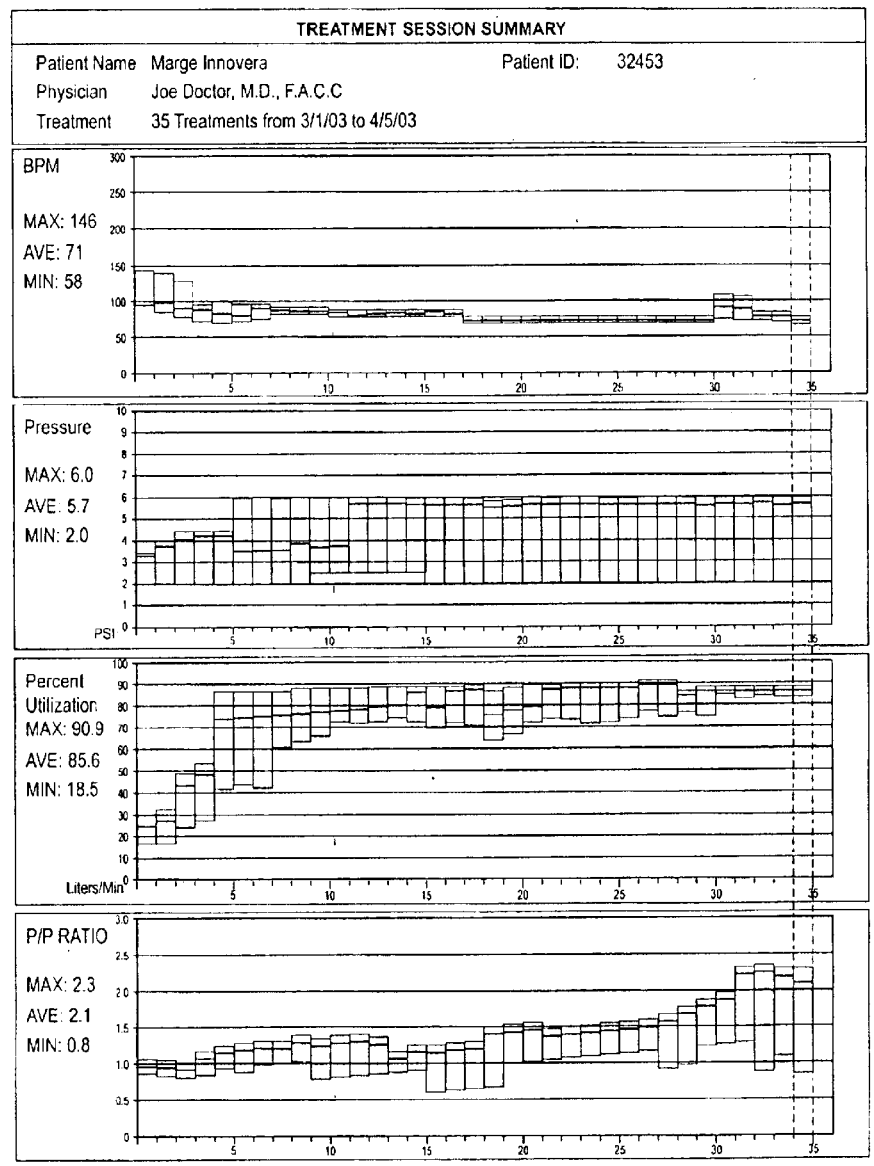
FIGS. 11, 12 and 13 are graphical displays of ECP system parameters and cardiac parameters for a complete course of ECP therapy.
Figure 12:
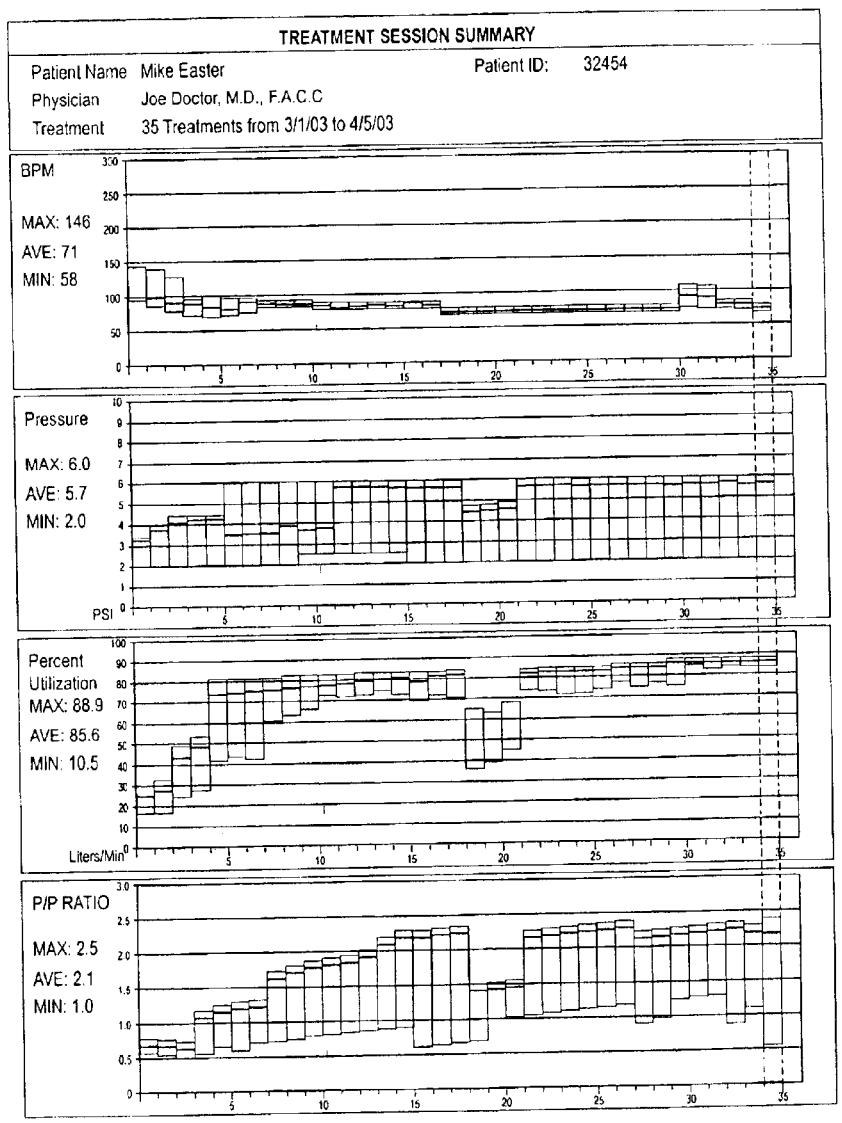
Figure 13:
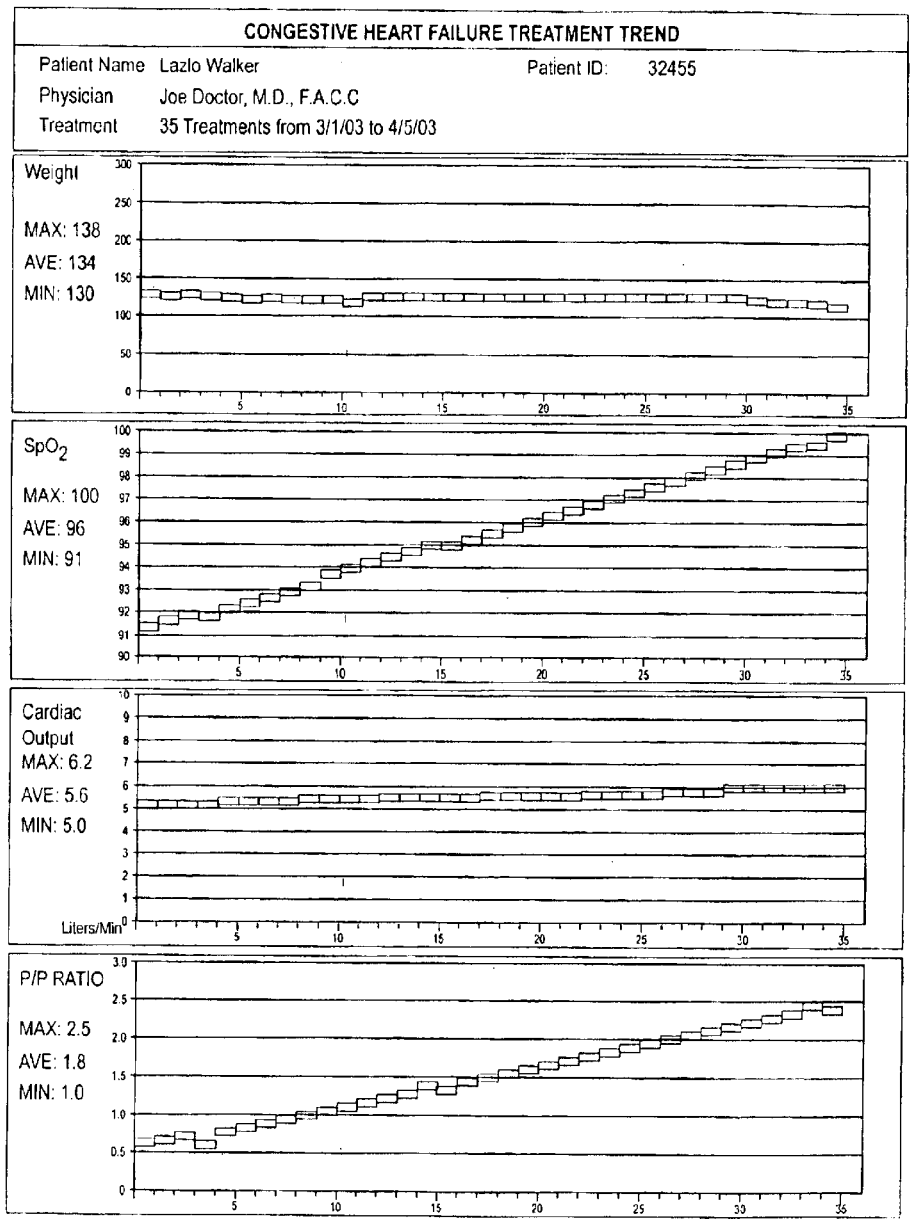

FIGS. 11 and 12 and 13 are graphical displays of ECP system parameters and cardiac parameters for a complete course of ECP therapy. FIG. 11 is a display summarizing heart rate data, cuff pressures, utilization percentages, and peak-to-peak ratios data over the course of 35 treatment sessions. As can be appreciated from the display, cuff pressure has been consistently high after ramping up during the initial sessions, the utilization percentage has been high after ramping up during the initial sessions. However, the peak-to-peak ratio achieved during therapy was sub-optimal during most of the therapy, and increased to effective levels only during the last several sessions. With this data collected and presented according to the display, the operator may establish a basis for continuing therapy beyond the standard 35-session therapy. FIG. 12 is a another display summarizing heart rate data, cuff pressures, utilization percentages, and peak-to-peak ratios data over the course of 35 treatment session of another patient. In this display, the percent utilization and peak-to-peak ratio are unexpectedly low for several sessions (sessions 19–21), and this can be traced to the lower cuff pressures recorded during those sessions. Again, this provides an objective basis for providing additional treatment sessions, so that the industry standard 35-session therapy actually comprises 35 effective session. FIG. 13 is a another display summarizing patient weight data, pulse oximetry data, cardiac output data and peak-to-peak ratios over the course of 35 treatment session of another patient. This display is particularly useful for CHF patients, as it display the pulse oximetry and cardiac output data from the patient, and as it is expected that these cardiac parameters should be improved by ECP, the display provides documentation of the effect on the patient.

In clinical use, the various reports are useful to monitor the proper performance of ECP during each session. The data is measured continuously and is provided to the operator for real time control of the therapy. A medical facility can thus control a number of ECP systems simultaneously, using a single operator, and a central control system. The central control system can obtain data and reports generated by each ECP system through networking means (local area networks, telemetry, wireless communications, internet communications, etc.) and exercise control of programmable variables through the same networking means, and exercise personal control over physical conditions, such as pad tightness, comfort pads, etc. In this system, any adjustments to the therapy that require a physician's input can be obtained without the need for a physician in immediate proximity to the patients.

The existence of conditions such as angina pectoris and congestive heart failure is indicated by self-reported symptoms, such as chest pain, shortness of breath, weight gain, etc. The ECP therapy leads to relief of these symptoms in most patients. To track these symptoms, the control system provides fields for input of patient reports of these symptoms as they exist prior to treatment, on a daily basis during treatment, and post-treatment. Congestive heart failure may also be objectively indicated by measurable cardiac parameters such as the ECG, blood pressure, blood flow sounds (indicative of poorly functioning heart valves, for example), and breathing sounds (indicative of fluid in the lungs) and cardiac output (volume of blood pumped per minute). To track these cardiac parameters, the control system provides fields for input of these parameters as they exist prior to treatment, on a daily basis during treatment, and post-treatment. Alleviation of the patient reported symptoms and improvement in the cardiac parameters may thus be tracked and correlated with ECP therapy performance. Additionally, broader experience with a number of patients, combined with ability to retrieve ECP system data and correlate with patient cardiac data, is expected to result in refinement of the therapy and statistically based enhancements and adjustments to ECP parameters.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A system for performing multiple sessions of external counterpulsion therapy on a patient and recording and presenting data relative to the therapy to an operator, said system comprising:

one or more inflatable bladders adapted to compress the patient;

and inflation system for inflating the inflatable bladders;

a blood pressure monitoring system operable to continuously detect the patient's blood pressure and transmit blood pressure data;

ECG monitoring system operable to continuously detect the patient's ECG and transmit ECG data;

a computerized control system operable to control the inflation system, receive and record ECG data from the ECG monitoring system, receive and record data from the blood pressure monitoring system; said control system programmed to operate the inflation system in response to the ECG data;

wherein the computerized control system is further programmed to:

present a first display comprising:
fields for entry of patient data and ECP system parameters applicable to the patient;
wherein for sessions subsequent to an initial session, the display is presented in a form containing values of patient data and ECP system parameters of a prior session;

record cardiac parameters for substantially the entirety of each treatment session;

present a second display comprising one or more trace data fields and present an ECG trace generated from the ECG data, a blood pressure trace generated from the blood pressure data, and an inflation/deflation data trace corresponding to the control system's operation of the inflation system in the trace data fields;

presenting substantially continuous ECG data, blood pressure data, and inflation/deflation data corresponding to the entirety of a treatment session in the trace data fields in the second display; wherein the control system is further programmed to calculate a utilization percentage corresponding to the percentage of available compression time during which the system inflates the bladders and present the utilization percentage within the first display.

2. A system for performing multiple sessions of external counterpulsion therapy on a patient and recording and presenting data relative to the therapy to an operator, said system comprising:

one or more inflatable bladders adapted to compress the patient;

and inflation system for inflating the inflatable bladders;

a blood pressure monitoring system operable to continuously detect the patient's blood pressure and transmit blood pressure data;

ECG monitoring system operable to continuously detect the patient's ECG and transmit ECG data;

a computerized control system operable to control the inflation system, receive and record ECG data from the ECG monitoring system, receive and record data from the blood pressure monitoring system; said control system programmed to operate the inflation system in response to the ECG data;

wherein the computerized control system is further programmed to:

present a first display comprising:
fields for entry of patient data and ECP system parameters applicable to the patient;
wherein for sessions subsequent to an initial session, the display is presented in a form containing values of patient data and ECP system parameters of a prior session;

record cardiac parameters for substantially the entirety of each treatment session;

present a second display comprising one or more trace data fields and present an ECG trace generated from the ECG data, a blood pressure trace generated from the blood pressure data, and an inflation/deflation data trace corresponding to the control system's operation of the inflation system in the trace data fields;

presenting substantially continuous ECG data, blood pressure data, and inflation/deflation data corresponding to the entirety of a treatment session in the trace data fields in the second display;

wherein the control system is further programmed to display substantially continuous ECG data, blood pressure data, and inflation/deflation data corresponding to entirety of treatment session in the second display in multiple display pages, with each display page displaying a portion of the single record; and the control system is further programmed to calculate a utilization percentage corresponding to the percentage of available compression time during which the system inflates the bladders and present the utilization percentage within the second display.

3. The system of claim 1 or 2 wherein the control system is further programmed to display a cursor in relationship to the trace data field and interpret operator manipulation of the cursor as input as to desired small time periods represented within the trace data field, and thereafter present a third display comprising an enlarged trace data field covering a time period consisting of the desired small time period.

4. The system of claim 3 wherein the control system is further programmed to present a plurality of cursors in logical proximity to the blood pressure trace, and interpret operator manipulation of the cursors as input as to operator determined systolic blood pressure, augmented diastolic blood pressure, and baseline blood pressure, and thereafter compute an augmentation ratio and display the augmentation ratio with the third display.

5. The system of claim 4 wherein the control system is further programmed to present a third display comprising a multi-session trend field: and present a graph of augmentation ratio per therapy session.

6. The system of claim 4 wherein the control system is further programmed to present a third display comprising a summary data for multiple sessions, and present a table of augmentation ratio per therapy session.

7. The system of claim 1 or 2 wherein the control system is further programmed to present a plurality of cursors in logical proximity to the blood pressure trace, and interpret operator manipulation of the cursors as input as to operator determined systolic blood pressure, augmented diastolic blood pressure, and baseline blood pressure, and thereafter compute an augmentation ratio and display the augmentation ratio.

8. The system of claim 7 wherein the control system is further programmed to present a third display comprising a multi-session trend field: and present a graph of augmentation ratio per therapy session.

9. The system of claim 8 wherein the control system is further programmed to present a session selection cursor within the fourth display and permit operator manipulation of the session selection cursor along the graph to locate the session selection cursor in logical relation to the therapy session numbers of the graph, and interpret operator manipulation of session selection cursor as selection of a particular session, and thereafter selectively present the second display or generate a fifth display comprising a graph of a cardiac parameter over time for the selected session.

10. The system of claim 7 wherein the control system is further programmed to present a third display comprising a summary data for multiple sessions, and present a table of augmentation ratio per therapy session.

11. The system of claim 10 wherein the control system is further programmed to present a session selection cursor within the fourth display and permit operator manipulation of the session selection cursor in the table to locate the session selection cursor in logical relation to the therapy session summary data, and interpret operator manipulation of session selection cursor as selection of a particular session, and thereafter selectively present the second display or generate a fifth display comprising a graph of a cardiac parameter over time for the selected session.

12. The system of claim 1 or 2 further comprising:
a central control system remotely locatable relative to the control system;
network means for transmitting cardiac parameters from the control systems to a central control system;
said central control system being operable to view the displays generated by the control system.

13. A system for performing multiple sessions of external counterpulsion therapy on a patient and recording and presenting data relative to the therapy to an operator, said system comprising:
one or more inflatable bladders adapted to compress the legs and buttocks of the patient;
and inflation system for inflating the inflatable bladders;
a blood pressure monitoring system operable to continuously detect the patient's blood pressure and transmit blood pressure data;
ECG monitoring system operable to continuously detect the patient's ECG and transmit ECG data;
a computerized control system operable to control the inflation system, receive and record ECG data from the ECG monitoring system, receive and record data from the blood pressure monitoring system; said control system programmed to operate the inflation system in response to the ECG data;

wherein the computerized control system is further programmed to:
present a first display comprising;
fields for entry of patient data including patient identification, size and tightness of bladders applied to the patient, and location of electrodes placed on the patient;
fields for entry of patient reported symptoms of chronic heart disease;
wherein for sessions subsequent to an initial session, the display is presented in a form containing values of patient data and patient reported symptoms of a prior session;
record cardiac parameters for substantially the entirety of each treatment session;
present a second display comprising one or more trace data fields and present an ECG trace generated from the ECG data, a blood pressure trace generated from the blood pressure data, and an inflation/deflation data trace corresponding to the control systems operation of the inflation system in the trace data fields;
presenting substantially continuous ECG data, blood pressure data, and inflation/deflation data corresponding to entirety of treatment session in the trace data fields in the second display; wherein
the control system is further programmed to calculate a utilization percentage corresponding to the percentage of available compression time during which the system inflates the bladders and present the utilization percentage within the first display.

14. A system for performing multiple sessions of external counterpulsion therapy on a patient and recording and presenting data relative to the therapy to an operator, said system comprising:
one or more inflatable bladders adapted to compress the legs and buttocks of the patient;
and inflation system for inflating the inflatable bladders;
a blood pressure monitoring system operable to continuously detect the patient's blood pressure and transmit blood pressure data;
ECG monitoring system operable to continuously detect the patient's ECG and transmit ECG data;
a computerized control system operable to control the inflation system, receive and record ECG data from the ECG monitoring system, receive and record data from the blood pressure monitoring system; said control system programmed to operate the inflation system in response to the ECG data;
wherein the computerized control system is further programmed to:
present a first display comprising;
fields for entry of patient data including patient identification, size and tightness of bladders applied to the patient, and location of electrodes placed on the patient;
fields for entry of patient reported symptoms of chronic heart disease;
wherein for sessions subsequent to an initial session, the display is presented in a form containing values of patient data and patient reported symptoms of a prior session;
record cardiac parameters for substantially the entirety of each treatment session;
present a second display comprising one or more trace data fields and present an ECG trace generated from the ECG data, a blood pressure trace generated from the blood pressure data, and an inflation/deflation data trace corresponding to the control systems operation of the inflation system in the trace data fields;

presenting substantially continuous ECG data, blood pressure data, and inflation/deflation data corresponding to entirety of treatment session in the trace data fields in the second display; wherein the control system is further programmed to display substantially continuous ECG data, blood pressure data, and inflation/deflation data corresponding to entirety of treatment session in the second display in multiple display pages, with each display page displaying portion of the single record; and the control system is further programmed to calculate a utilization percentage corresponding to the percentage of available compression time during which the system inflates the bladders and present the utilization percentage within the second display.

15. The system of claim 13 or 14 wherein the control system is further programmed to display a cursor in relationship to the trace data field and interpret operator manipulation of the cursor as input as to desired small time periods represented within the trace data field, and thereafter present a third display comprising an enlarged trace data field covering a time period consisting of the desired small time period.

16. The system of claim 13 or 14 wherein the control system is further programmed to present a plurality of cursors in logical proximity to the blood pressure trace, and interpret Operator manipulation of the cursors as input as to operator determined systolic blood pressure, augmented diastolic blood pressure, and baseline blood pressure, and thereafter compute an augmentation ratio and display the augmentation ratio.

17. The system of claim 15 wherein the control system is further programmed to present a plurality of cursors in logical proximity to the blood pressure trace, and interpret operator manipulation of the cursors as input as to operator determined systolic blood pressure, augmented diastolic blood pressure, and baseline blood pressure, and thereafter compute an augmentation ratio and display the augmentation ratio with the third display.

18. The system of claim 13 or 14 wherein the control system is further programmed to present a fourth display comprising a summary data for multiple sessions, and present a table of augmentation ratio per therapy session.

19. The system of claim 18 wherein the control system is further programmed to present a session selection cursor within the fourth display and permit operator manipulation of the session selection cursor in the table to locate the session selection cursor in logical relation to the therapy session summary data, and interpret operator manipulation of session selection cursor as selection of a particular session, arid thereafter selectively present the second display or generate a fifth display comprising a graph of a cardiac parameter over time for the selected session.

20. The system of claim 13 or 14 further comprising:
a central control system remotely locatable relative to the control system;
network means for transmitting cardiac parameters from the control systems to a central control system;
said central control system being operable to view the displays generated by the control system.

21. A system for performing multiple sessions of external counterpulsion therapy on a patient and recording and presenting data relative to the therapy to an operator, said system comprising:
one or more inflatable bladders adapted to compress the legs and buttocks of the patient;
and inflation system for inflating the inflatable bladders;
a blood pressure monitoring system operable to continuously detect the patient's blood pressure and transmit blood pressure data;
ECG monitoring system operable to continuously detect the patient's ECG and transmit ECG data;
a computerized control system operable to control the inflation system, receive and record ECG data from the ECG monitoring system, receive and record data from the blood pressure monitoring system; said control system programmed to operate the inflation system in response to the ECG data;
wherein the computerized control system is further programmed to:
present a first display comprising;
fields for entry of patient data including patient identification, size and tightness of bladders applied to the patient, and location of electrodes placed on the patient;
fields for entry of patient reported symptoms of chronic heart disease;
wherein for sessions subsequent to an initial session, the display is presented in a form containing values of patient data and patient reported symptoms of a prior session;
record cardiac parameters for substantially the entirety of each treatment session;
present a second display comprising one or more trace data fields and present an ECG trace generated from the ECG data, a blood pressure trace generated from the blood pressure data, and an inflation/deflation data trace corresponding to the control systems operation of the inflation system in the trace data fields;
present substantially continuous ECG data, blood pressure data, and inflation/deflation data corresponding to entirety of treatment session in the trace data fields in the second display;
wherein the control system is further programmed to present a plurality of cursors in logical proximity to the blood pressure trace, and interpret operator manipulation of the cursors as input as to operator determined systolic blood pressure, augmented diastolic blood pressure, and baseline blood pressure, and thereafter compute an augmentation ratio and display the augmentation ratio.

22. The system of claim 21 wherein:
the control system is further programmed to display substantially continuous ECG data, blood pressure data, and inflation/deflation data corresponding to entirety of treatment session in the second display in multiple display pages, with each display page displaying portion of the single record.

23. A system for performing multiple sessions of external counterpulsion therapy on a patient and recording and presenting data relative to the therapy to an operator, said system comprising:
one or more inflatable bladders adapted to compress the legs and buttocks of the patient;
and inflation system for inflating the inflatable bladders;
a blood pressure monitoring system operable to continuously detect the patients blood pressure and transmit blood pressure data;

ECG monitoring system operable to continuously detect the patient's ECG and transmit ECG data;

a computerized control system operable to control the inflation system, receive and record ECG data from the ECG monitoring system, receive and record data from the blood pressure monitoring system; said control system programmed to operate the inflation system in response to the ECG data;

wherein the computerized control system is further programmed to:

present a first display comprising;
    fields for entry of patient data including patient identification, size and tightness of bladders applied to the patient, and location of electrodes placed on the patient;

fields for entry of patient reported symptoms of chronic heart disease;

wherein for sessions subsequent to an initial session, the display is presented in a form containing values of patient data and patient reported symptoms of a prior session;

record cardiac parameters for substantially the entirety of each treatment session;

present a second display comprising one or more trace data fields and present an ECG trace generated from the ECG data, a blood pressure trace generated from the blood pressure data, and an inflation/deflation data trace corresponding to the control systems operation of the inflation system in the trace data fields;

present substantially continuous ECG data, blood pressure data, and inflation/deflation data corresponding to entirety of treatment session in the trace data fields in the second display;

wherein the control system is further programmed to present a third display comprising a summary data for multiple sessions, and present a table of augmentation ratio per therapy session.

24. The system of claim 23 wherein:

the control system is further programmed to display substantially continuous ECG data, blood pressure data, and inflation/deflation data corresponding to entirety of treatment session in the second display in multiple display pages, with each display page displaying portion of the single record.

* * * * *